(12) United States Patent
Shani et al.

(10) Patent No.: US 10,271,776 B2
(45) Date of Patent: Apr. 30, 2019

(54) COMPUTER AIDED ANALYSIS AND MONITORING OF MOBILITY ABNORMALITIES IN HUMAN PATIENTS

(76) Inventors: Mordechai Shani, Ramat-Efal (IL); Yoram Feldman, Tel-Mond (IL)

( * ) Notice: Subject to any disclaimer, the term of this patent is extended or adjusted under 35 U.S.C. 154(b) by 595 days.

(21) Appl. No.: 13/883,012

(22) PCT Filed: Nov. 3, 2011

(86) PCT No.: PCT/IB2011/054901
§ 371 (c)(1),
(2), (4) Date: May 2, 2013

(87) PCT Pub. No.: WO2012/059883
PCT Pub. Date: May 10, 2012

(65) Prior Publication Data
US 2013/0226039 A1 Aug. 29, 2013

Related U.S. Application Data

(60) Provisional application No. 61/410,028, filed on Nov. 4, 2010.

(51) Int. Cl.
*A61B 5/11* (2006.01)
*G06F 19/00* (2018.01)
*A61B 5/00* (2006.01)

(52) U.S. Cl.
CPC ........ *A61B 5/1128* (2013.01); *G06F 19/3418* (2013.01); *A61B 5/0022* (2013.01); *A61B 5/1126* (2013.01); *A61B 5/4833* (2013.01)

(58) Field of Classification Search
CPC ..... A61B 5/4528; A61B 5/103; A61B 5/0053; A61B 5/1071

(Continued)

(56) References Cited

U.S. PATENT DOCUMENTS 6,007,459 A 12/1999 Burgess
6,063,046 A 5/2000 Allum
(Continued)

FOREIGN PATENT DOCUMENTS

EP 1970005 9/2008
WO WO 2007-113890 10/2007
WO WO 2008-129442 10/2008

OTHER PUBLICATIONS

International Search Report of PCT Application No. PCT/IB2011/054901 dated Jun. 6, 2012.

*Primary Examiner* — Daniel L Cerioni
(74) *Attorney, Agent, or Firm* — Pearl Cohen Zedek Latzer Baratz LLP

(57) ABSTRACT

A method for analyzing and monitoring mobility abnormalities of human patients is provided herein. The method includes the following stages: capturing a physiotherapeutic sequence of a scene that includes 3D positioning and orientations of the body parts of the human patient over time; monitoring, over a physiotherapeutic session, the set of key points on the human patient while the human patient performs physiotherapeutic exercises comprising a set of predefined sequences of body-related and limb-related postures and gestures; and analyzing the monitored set of key points during the physiotherapeutic session, to yield an assessment of a level of compliance of the human patient in performing the physical training or physiotherapeutic exercises, based at least partially on the abnormality mobility profile. Additionally, an analysis during the physiotherapeutic session may be carried out, to yield an assessment of a level of compliance of the human patient in performing specified physiotherapeutic exercises.

8 Claims, 5 Drawing Sheets

(58) Field of Classification Search
USPC .................................................. 600/587, 595
See application file for complete search history.

(56) References Cited

U.S. PATENT DOCUMENTS

| | | | |
|---|---|---|---|
| 6,666,831 | B1 | 12/2003 | Edgerton et al. |
| 7,825,815 | B2 | 11/2010 | Shears et al. |
| 2006/0183980 | A1 | 8/2006 | Yang |
| 2007/0250134 | A1 | 10/2007 | Miesel et al. |
| 2007/0287900 | A1* | 12/2007 | Breen .................. A61B 5/1116 600/407 |
| 2008/0045804 | A1 | 2/2008 | Williams |
| 2008/0091373 | A1 | 4/2008 | McGibbon et al. |
| 2008/0119763 | A1* | 5/2008 | Wiener .................. A61B 5/224 600/587 |
| 2009/0030289 | A1 | 1/2009 | Katayama et al. |
| 2010/0117837 | A1* | 5/2010 | Stirling ................ A61B 5/1127 340/573.1 |
| 2011/0264010 | A1 | 10/2011 | Williams |
| 2014/0153794 | A1* | 6/2014 | Varaklis ............... A61B 5/1124 382/128 |

* cited by examiner

_300B_

340 — CAPTURING A PHYSIOTHERAPEUTIC SEQUENCE OF A SCENE THAT INCLUDES 3D POSITIONING AND ORIENTATIONS OF THE BODY PARTS OF THE HUMAN PATIENT OVER TIME

350 — MONITORING, OVER A PHYSIOTHERAPEUTIC SESSION, THE SET OF KEY POINTS ON THE HUMAN PATIENT WHILE THE HUMAN PATIENT PERFORMS PHYSIOTHERAPEUTIC EXERCISES COMPRISING A SET OF PREDEFINED SEQUENCES OF BODY-RELATED AND LIMB-RELATED POSTURES AND GESTURES

360 — ANALYZING THE MONITORED SET OF KEY POINTS DURING THE PHYSIOTHERAPEUTIC SESSION, TO YIELD AN ASSESSMENT OF A LEVEL OF COMPLIANCE OF THE HUMAN PATIENT IN PERFORMING THE PHYSIOTHERAPEUTIC EXERCISES, BASED AT LEAST PARTIALLY ON THE ABNORMALITY MOBILITY PROFILE

370 — (OPTIONAL) PROVIDING A QUANTITATIVE SCORE INDICATIVE OF THE HUMAN PATIENT COMPLIANCE WITH THE PHYSIOTHERAPEUTIC SESSION, WHEREIN THE SCORE IS BASED ON A COMPARISON TO A PREDEFINED DATABASE

380 — (OPTIONAL) PROVIDING AT LEAST ONE OF: FEEDBACK, EXERCISE ADJUSTMENTS, AND RECOMMENDATIONS TO THE HUMAN PATIENT, BASED ON THE ASSESSMENT OF THE LEVEL OF COMPLIANCE OF THE HUMAN PATIENT IN PERFORMING THE PHYSIOTHERAPEUTIC EXERCISES

Figure 4

COMPUTER AIDED ANALYSIS AND MONITORING OF MOBILITY ABNORMALITIES IN HUMAN PATIENTS

CROSS-REFERENCE TO RELATED APPLICATIONS

This application is a National Phase Application of PCT International Application No. PCT/IB2011/054901, International Filing Date Nov. 3, 2011, entitled "COMPUTER AIDED ANALYSIS AND MONITORING OF MOBILITY ABNORMALITIES IN HUMAN PATIENTS", published on May 2, 2012 as International Publication Number WO 2012/059883, claiming priority of US Provisional Patent Application No. 61/410,028, filed Nov. 4, 2010, both of which are incorporated herein by reference in their entirety.

BACKGROUND

1. Technical Field

The present invention relates to analyzing and monitoring mobility abnormalities of human patients and more specifically, to such analysis and monitoring that is carried out for physical training or physiotherapeutic purposes.

2. Discussion of the Related Art

During the last decades, the demand for physical therapy services constantly rises. In a typical physical therapy session, a clinician (or a human expert) assesses a patient's biomechanical abilities or disabilities by reviewing relevant medical records and by direct observation of the patient. Often the clinician's remedial techniques include hands-on treatment. Such treatment may include massage, joint manipulation and postural adjustments. Often the patient's response to hands-on treatment is used to enable the clinician to further understand, and remedy the patient's condition.

Various techniques of providing physical therapy are taught to and typically used by physical therapists. These techniques are implemented through multiple of named physical therapy systems.

More recently, various systems that allow monitoring remote physiotherapy sessions have been developed. For example, U.S. Pat. No. 6,007,459 describes a method and system for providing physical therapy to a human client having a physical condition includes the steps of providing an electronic communication link between the patient and a clinician, instructing the patient to move in a particular manner, or to assume a sustained posture or perform a test. Then, feedback is requested from the patient. The feedback relates to bodily sensation corresponding to the movement or sustained posture and can be audio, video, and/or data type feedback. The communication link communicates the feedback to the clinician. Accordingly, the clinician utilizes the feedback to assess the physical condition of the patient. The clinician also communicates remedial movements or a remedial sustained posture to the patient to address the physical condition. Various postural measurements and testing devices may be used in conjunction with the present invention to facilitate assessment and help address the physical condition in accordance with accepted physical therapy techniques.

Another exemplary system is described in International Patent Application Publication Number WO 2007/113890 which described how by means of a computer network, preferably consisting of portable computers, connected telemetrically in a known way to a central server equipped with, or connected to, a database, the provider of rehabilitative care and the patient are connected together and with other portable computers, which can send, receive and analyze data in the form of hypertext, video, and audio data; in particular, each computer enabled can connect up to the database for control of the recorded data. With an appropriate software residing in the server, there are sent automatically, in response to received hypertext, video, and audio data (obtained from the patient), other hypertext, video, and audio data constituted by guidelines for rehabilitation, indications for kinesio-physiotherapy treatments, and/or other modes of intervention. The method envisages that at the start of, during, and at the end of the therapy in question, the film of a test is made. This film is recorded, in the form of a video-audio clip, in a purposely provided user directory in the central database, to enable remote monitoring of the results of the rehabilitation therapy.

BRIEF SUMMARY

One aspect of the present invention provides a method of analyzing mobility abnormalities of human patients. The method includes the following stages: capturing a physical training or physiotherapeutic sequence of a scene that includes 3D positioning and orientations of the body parts of the human patient over time; monitoring, over a physiotherapeutic session, the set of key points on the human patient while the human patient performs physiotherapeutic exercises comprising a set of predefined sequences of body-related and limb-related postures and gestures; and analyzing the monitored set of key points during the physiotherapeutic session, to yield an assessment of a level of compliance of the human patient in performing the physiotherapeutic exercises, based at least partially on the abnormality mobility profile.

Another aspect of the present invention provides a method of monitoring compliance of human patients with sets of physical training or physiotherapeutic exercises that have been tailored specifically for their needs. The method includes the following stages: capturing a physiotherapeutic sequence of a scene that includes 3D positioning and orientations of body parts of a human patient over time; monitoring, during a physiotherapeutic session, a set of key points on the human patient while the human patient performs physical training or physiotherapeutic exercises comprising a set of predefined sequences of body-related and limb-related postures and gestures; and analyzing the monitored set of key points in the physical training or physiotherapeutic session, to yield an assessment of a physiotherapeutic condition of the human patient, based at least partially on an abnormality mobility profile of the human patient, wherein the abnormality mobility profile is indicative of mobility limitations and abnormalities of the human patient in terms of body-related and limb-related postures and gestures.

Other aspects of the invention may include systems arranged to execute the aforementioned methods and a computer readable program configured to execute the aforementioned methods. These, additional, and/or other aspects and/or advantages of the embodiments of the present invention are set forth in the detailed description which follows; possibly inferable from the detailed description; and/or learnable by practice of the embodiments of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 4 shows a high level flowchart depicting another aspect of a method according to some embodiments of the invention;

Figure 1:
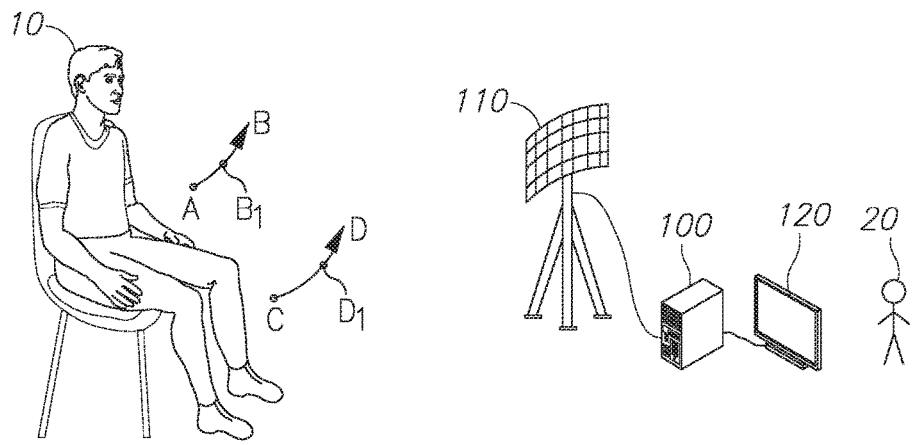
FIG. 1 is a high level schematic block diagram illustrating a calibration environment of the system according to some embodiments of the invention.

The drawings together with the following detailed description make apparent to those skilled in the art how the invention may be embodied in practice.

DETAILED DESCRIPTION

Prior to setting forth the detailed description, it may be helpful to set forth definitions of certain terms that will be used hereinafter.

The term "3D positioning" as used herein refers to a comprehensive spatial representation of the body parts of a human patient that is sufficient to describe the postures and the gestures of the human patient. 3D positioning may be carried out using vectors but may alternatively be described in other forms of 3D representation.

The term "abnormality mobility profile" as used herein refers to a set of deviations from a normal mobility profile attributed to healthy persons. The deviations represent limitations imposed on a human patients in terms of his or her ability to carry out any posture or gesture selected from a specific set of postures and gestures.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 is a high level schematic block diagram illustrating a calibration environment of the system according to some embodiments of the invention. The calibration systems includes one or more sensors 110 configured to capture, in a calibration sequence, 3D positioning and orientation of limbs of a human patient 10, wherein the human patient is instructed to follow a sequence of movements in a calibration session. Such movement may include, for example, moving his or her left hand upwards from point A to B or moving his or her left leg upwards from point C to D. By way of illustration, due to some abnormality, human patient 10 can only follow the calibration exercise to some extent, to points B' and D', respectively.

The system further include a processing unit 100 configured to monitor, over the calibration session, a set of key points, wherein at least some of the key points are positioned in predefined locations on the limbs of human patient 10. Processing unit 100 is further configured to generate an abnormality mobility profile of human patient 10 by analyzing the monitored set of key points in view of deviations from a predefined normal mobility profile of a healthy human positioned in the predefined posture, wherein the abnormality mobility profile is indicative of mobility limitations and abnormalities of the human patient in terms of body-related and limb-related postures and gestures.

Consistent with some embodiments of the present invention, during the calibration session, the human patient is instructed to perform a set of predefined sequences of postures and gestures and wherein the processor is configured to generate the abnormality mobility profile at least partially based on a comparison between the monitored key points of the human patient responsive to the predefined sequences of postures and gestures and respective monitored key points of the healthy human responsive to the predefined sequences of postures and gestures.

In some embodiments, the presence or absence of one or more biomechanical abnormalities, such as unwanted compensatory movements and their degree, are determined according to a 3D motion analysis of the set of 3D movement vectors. Optionally, the 3D motion analysis is set to detect limb movement along a 3D path that is set to measure the range of motion (ROM), speed, acceleration, time to reach max speed, time to reach max range of motion, measured compensation motions while in motion, and/or coordination of the limbs, head, torso and other body parts. Consistent with some embodiments of the present invention, the abnormality mobility profile may be achieved by comparing between a 3D path set by the calculated vectors and a reference 3D path, for example a reference path set according to an exercise for evaluating the range of motion, the strength, and/or the coordination of a limb. For example, the reference 3D path may be of an exercise for evaluating the range of motion in a shoulder flexion, shoulder abduction and elbow flexion range of motion exercises as well as other body motions. By analyzing deviation between a reference 3D path and a performed 3D path, unwanted compensatory movements accompanying a practiced movement may be detected. For example, shoulder flexion (SF), shoulder elevation (SE), shoulder rotation (SR), shoulder abduction (SA), elbow flexion (EF) and trunk forward displacement (TF), trunk backward displacement (TB), trunk right displacement (TR) and trunk left displacement (TL), shoulder abduction and elbow flexion can also be detected as compensatory movements when present.

In some embodiments, calibration system includes one or more sensors (not shown) configured to capture, in a calibration sequence, 3D positioning and orientation of limbs of a human patient, wherein the human patient is instructed to follow a sequence of movements in a calibration session;

and a monitoring module configured to: monitor, over the calibration session, a set of key points, wherein at least some of the key points are positioned in predefined locations on the limbs of the human patient, and generate an abnormality mobility profile of the human patient by analyzing the monitored set of key points in view of deviations from a predefined normal mobility profile of a healthy human positioned in the predefined posture, wherein the abnormality mobility profile is indicative of mobility limitations and abnormalities of the human patient in terms of body-related and limb-related postures and gestures.

Consistent with some embodiments of the present invention, the processor is further configured to semi automatically generate a set of physical training or physiotherapeutic exercises tailored for the human patient's motor capabilities, based on the abnormality mobility profile and additional input from a human expert.

Figure 2:
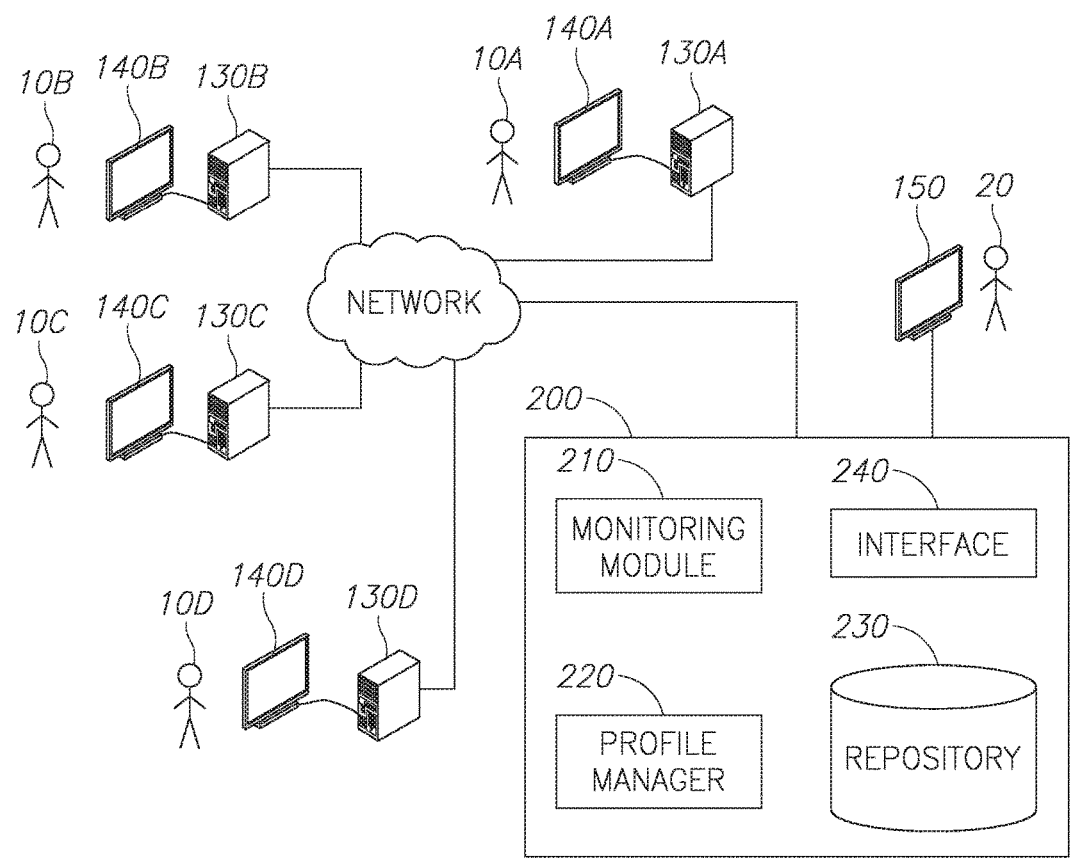
FIG. 2 is a high level schematic block diagram illustrating a system according to some embodiments of the invention.

FIG. 2 is a high level schematic block diagram illustrating a computer aided remote physical training or physiotherapeutic system according to some embodiments of the invention. The remote physiotherapeutic system is configured to monitor a plurality of remote physiotherapy sessions, such as exercise physiotherapy sessions and/or diagnostic physiotherapy sessions, according to some embodiments of the present invention. The system includes a central terminal 200, implemented on one or more servers, which communicates with a plurality of client terminals 130A-D, each manages a different remote physiotherapy session. Each one of client terminals 130A-D, for example a laptop, a desktop, a tablet, a cellular phone, a Smartphone, or any other computing unit, is connected to an image capturing unit (not shown), such as a web camera, which includes one or more image sensors. As the client terminals 130A-D are connected via a network, they may be placed in different households, different rooms, and/or in any of a plurality of different geographic locations. The display 140A-D of the client terminals 130A-D is optionally a two dimensional (2D) display, such as a liquid crystal display (LCD) or a three dimensional (3D) display, such as an Anaglyphic 3D display, a Polarization 3D display, and an alternate-frame sequencing display. The image capturing unit (not shown) may be a 3D camera or a 3D web camera, for example as Minoru™ 3.0.1 which captures 3D images or a 2D camera or a 2D web camera which captures 2D images. It should be noted that the capturing can be carried out in any spectral range and may include non visible spectrum and other types of waves that electromagnetic waves such as ultra sound waves.

The type of the captured images changes the image processing process that is described below. Each one of client terminals 130A-D manages and displays a virtual environment that allows the patient to interact with simulated elements, for example during a game and/or a virtual challenge, using natural human hand and body motions. The virtual environment may be managed locally, for example by a local physiotherapy session module (not shown) which is hosted by the client terminal 140A-D and/or remotely, for example by a physiotherapy session server (not shown) that is connected to the network and accessed by the client terminals 140A-D, for example via a designated website or portal. In such an embodiment, the game challenge and/or virtual challenge motivate the patient to perform the gestures in a more accurate manner so as to proceed in a certain game plot or to achieve a higher score. The patient's attention is diverted from the burden of performing the physical operation gestures, thus encourages more repetitions, distraction from pain, and improves performance, for example increases the range of motion.

Consistent with some embodiments of the invention, during the calibration session, the human patient is instructed to perform a set of predefined sequences of postures and gestures and wherein the processor is configured to generate the abnormality mobility profile at least partially based on a comparison between the monitored key points of the human patient responsive to the predefined sequences of postures and gestures and respective monitored key points of the healthy human responsive to the predefined sequences of postures and gestures.

Consistent with some embodiments of the invention, the processor is further configured to semi automatically generate a set of physiotherapeutic exercises tailored for the human patient's motor capabilities, based on the abnormality mobility profile and additional input from a human expert.

According to some embodiments of the present invention, the selected physical tasks are set to test the cognitive skills and/or to practice the cognitive skills of the patient. For example, when the patient has to move a number of virtual objects from one place to another, it is required to select them in a logical order and/or to assemble a certain combination therefrom. The logical order is indicative of cognitive abilities.

The client terminals 130A-D communicate with the central terminal 200 via the network 50, allowing the central terminal 200 to receive data therefrom. As used herein a network means a communication network, such as a computer network, for example the Internet. Optionally, the central terminal 200 includes an interface 240 that is connected to communicate with each client terminal 130A-D. The interface 240 optionally includes a network interface card (NIC) or a modem device which receives data, for example alarms or biomechanical abnormality information, from each one of the client terminals 130A-D, for example as described below. central terminal 200 further includes profile manager 220, monitoring module 210, and repository 230.

Each one of client terminals 130A-D allows one or more remote clinician terminal(s) 20 and/or a monitoring module 210 to participate in one or more of the physiotherapy sessions which are managed and displayed by the various client terminals 130A-D, for example as described below. Optionally, the monitoring module 210 communicates with the local physiotherapy session modules in a bidirectional connection, In such an embodiment, the monitoring module 210 may send instructions to a local physiotherapy session module for changing one or more characteristics of the local physiotherapy session, for example a difficulty degree, an exercise type, and/or any characteristic of the virtual environment or simulated objects. These instructions may be send in response to input from a clinician, such as a therapist, that reviews the performance of the patient from a remote clinician terminal 150 and/or from an automatic analysis of the performance of the patient by monitoring module 210.

Consistent with some embodiments of the invention, the calibration system and the physiotherapeutic system can be combined together. Thus, physiotherapeutic system will include one or more sensors configured to capture a physiotherapeutic sequence of a scene that includes 3D positioning and orientations of the limbs of the human patient over time; and a processor configured to: monitor, over a physiotherapeutic session, the set of key points on the human patient while the human patient performs physiotherapeutic exercises comprising a set of predefined sequences of body-related and limb-related postures and gestures; and analyze the monitored set of key points in the physiotherapeutic session, to yield an assessment of a physiotherapeutic condition of the human patient, based at least partially on the abnormality mobility profile.

Consistent with some embodiments of the invention, the one or more sensors configured to capture the physiotherapeutic sequence and the processor configured to analyze the monitored set of key points in the physiotherapeutic session is positioned at different locations.

Consistent with some embodiments of the invention, the capturing of the physiotherapeutic sequence is carried out simultaneously at a plurality of different locations, wherein in each one of different locations, a different human patient is following a tailored set of exercises, and wherein the assessment of the physiotherapeutic condition of at least some of the different human patients is presented to a human expert in real time.

Each client terminal monitors a patient by using a simple image capturing unit, such as a 2D or 3D web camera, to capture images of his physical operations and by a motion analysis module which analyses the captured images. These systems and methods allow the clinician to prescribe therapeutic exercises to be performed at home while it reliably and accurately monitors and corrects the performance level of each patient in real-time.

According to some embodiments of the present invention, there is provided a method of managing a plurality of remote physiotherapy sessions. The method is based on a plurality of virtual environments which are managed on a plurality of client terminals and/or by a central unit. The virtual environments allow a plurality of patients to interact simultaneously therewith. Each patient interacts with a respective virtual environment by performing a plurality of physical operations, such as physiotherapy gestures, to affect one or more simulated virtual elements. The patient is monitored by a client terminal when he performs the physical operations so as to evaluate a level of biomechanical abnormality in his movements. This evaluation of the movements of the users allow a remote user, such as a therapist, to determine whether to intervene by communicating with the patient, for example by instant messaging, video call and/or audio call, or not. The communication may to provide instructions, a positive feedback, a negative feedback, changing a difficulty level, and/or type of exercise, and/or to schedule a meeting.

In such a manner, a single therapist may monitor a plurality of remote physiotherapy sessions which occur simultaneously and prioritize his involvement in each one of the physiotherapy sessions.

Consistent with some embodiments of the invention, wherein the processor configured to analyze the monitored set of key points in the physiotherapeutic session is further configured to provide a quantitative score indicative of the human patient advancement responsive to the physiotherapeutic session, wherein the score is based on a comparison to a predefined database.

Consistent with some embodiments of the invention, comprising a user interface, wherein the processor configured to analyze the monitored set of key points in the physiotherapeutic session is further configured to provide, via the user interface, at least one of: feedback and recommendations to the human patient, based on the assessment of the physiotherapeutic condition thereof.

Consistent with some embodiments of the invention, wherein the presenting of the assessment of the physiotherapeutic condition of at least some of the different human patients is carried out in accordance of a dynamic prioritization process.

Consistent with some embodiments of the invention, the abnormality mobility profile of the human patient takes into account a complete representation of skeleton trajectories of the human patient, such that the feedback and the recommendations only promote exercises that are beneficial for the physiotherapeutic session of the human patient.

Advantageously, embodiments of the present invention allow human expert 20 to monitor, possibly from remote terminal 150, a plurality of patients which simultaneously perform different and/or similar physiotherapy sessions, optionally in their household, for example without a clinician. Some embodiments allow human expert 20 to determine whether to intervene with any of the physiotherapy sessions based on an automatic analysis of their performances. Optionally, the patients perform the physiotherapy sessions by interacting with client terminals which manage virtual environments, such as games, with which patients interact by performing physical operations.

Figure 3:
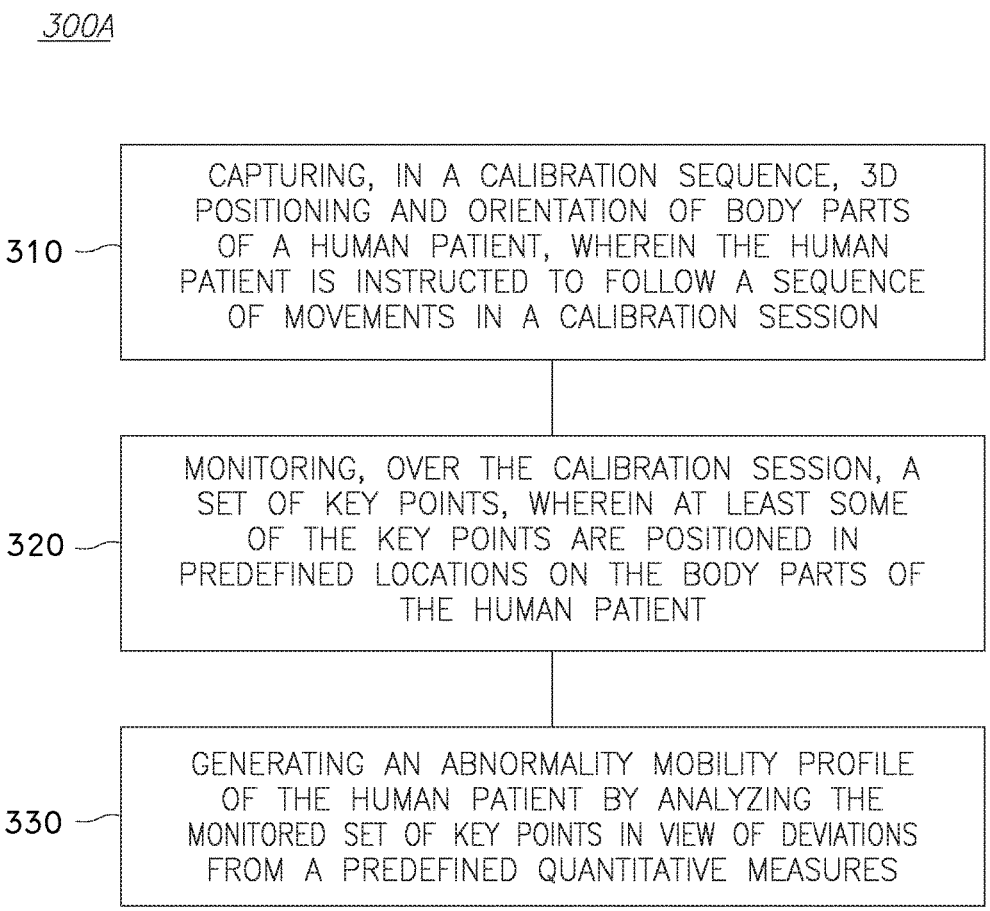
FIG. 3 shows a high level flowchart depicting an aspect of a method according to some embodiments of the invention.

FIG. 3 shows a high level flowchart depicting an aspect of a method according to some embodiments of the invention. Method 300 includes the following stages: capturing 310, in a calibration sequence, 3D positioning and orientation of body parts of a human patient, wherein the human patient is instructed to follow a sequence of movements in a calibration session; monitoring 320, over the calibration session, a set of key points, wherein at least some of the key points are positioned in predefined locations on the body parts of the human patient, and generating 330 an abnormality mobility profile of the human patient by analyzing the monitored set of key points in view of deviations from a predefined quantitative measures.

Consistent with some embodiments of the invention, during the calibration session, the human patient is instructed to perform a set of predefined sequences of postures and gestures and wherein the abnormality mobility profile is generated at least partially based on a comparison between the calibrated key points of the human patient responsive to the predefined sequences of postures and gestures and respective monitored key points of the healthy human responsive to the predefined sequences of postures and gestures.

Consistent with some embodiments of the invention, the method further includes the stage of semi automatically generating a set of physiotherapeutic exercises tailored for the human patient's motor capabilities based on the abnormality mobility profile and additional input from a human expert.

FIG. 4 shows a high level flowchart depicting another aspect of a method according to some embodiments of the invention. Consistent with some embodiments of the invention, method 300 further includes the stage of capturing 340 a physiotherapeutic sequence of a scene that includes 3D positioning and orientations of the body parts of the human patient over time; monitoring 350, over a physiotherapeutic session, the set of key points on the human patient while the human patient performs physiotherapeutic exercises comprising a set of predefined sequences of body-related and limb-related postures and gestures; and analyzing 360 the monitored set of key points during the physiotherapeutic session, to yield an assessment of a level of compliance of the human patient in performing the physiotherapeutic exercises, based at least partially on the abnormality mobility profile.

Consistent with some embodiments of the invention, the capturing of the physiotherapeutic sequence and the analyzing of the monitored set of key points during the physiotherapeutic session are carried out at different locations.

Consistent with some embodiments of the invention, the capturing of the physiotherapeutic sequence is carried out at one or more different locations, wherein in each one of the different locations, a different human patient is following a tailored set of exercises, and wherein the assessment of at least some of the different human patients is presented to a human expert in real time.

Consistent with some embodiments of the invention, method 300 further includes the stage of providing 370 a quantitative score indicative of the human patient compliance with the physiotherapeutic session, wherein the score is based on a comparison to a predefined database.

Consistent with some embodiments of the invention, the method 300 further includes the stage of providing 380 at least one of: feedback, exercise adjustments, and recommendations to the human patient, based on the assessment of the level of compliance of the human patient in performing the physiotherapeutic exercises.

Consistent with some embodiments of the invention, the presenting of the assessment of level of compliance of the human patient in performing the physiotherapeutic exercises of at least some of the different human patients is carried out in accordance of a dynamic prioritization process.

Consistent with some embodiments of the invention, the abnormality mobility profile of the human patient takes into account a complete representation of skeleton trajectories of the human patient, such that the feedback, the exercise adjustments, and the recommendations only promote exercises that are beneficial for the physiotherapeutic session of the human patient.

Figure 5:
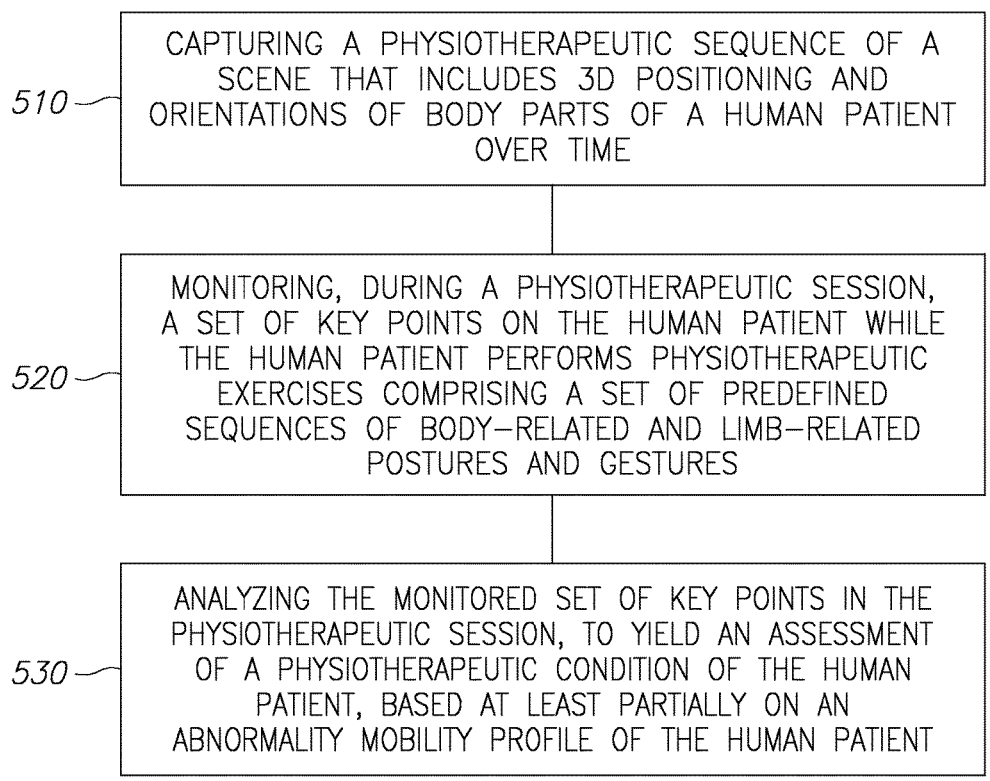
FIG. 5 shows a high level flowchart depicting yet another aspect of a method according to some embodiments of the invention.

FIG. 5 shows a high level flowchart depicting yet another aspect of a method according to some embodiments of the invention. Method 500 includes: capturing 510 a physiotherapeutic sequence of a scene that includes 3D positioning and orientations of body parts of a human patient over time; monitoring 520, during a physiotherapeutic session, a set of key points on the human patient while the human patient performs physiotherapeutic exercises comprising a set of predefined sequences of body-related and limb-related postures and gestures; and analyzing 530 the monitored set of key points in the physiotherapeutic session, to yield an assessment of a physiotherapeutic condition of the human patient, based at least partially on an abnormality mobility profile of the human patient, wherein the abnormality mobility profile is indicative of mobility limitations and abnormalities of the human patient in terms of body-related and limb-related postures and gestures.

Figure 6:
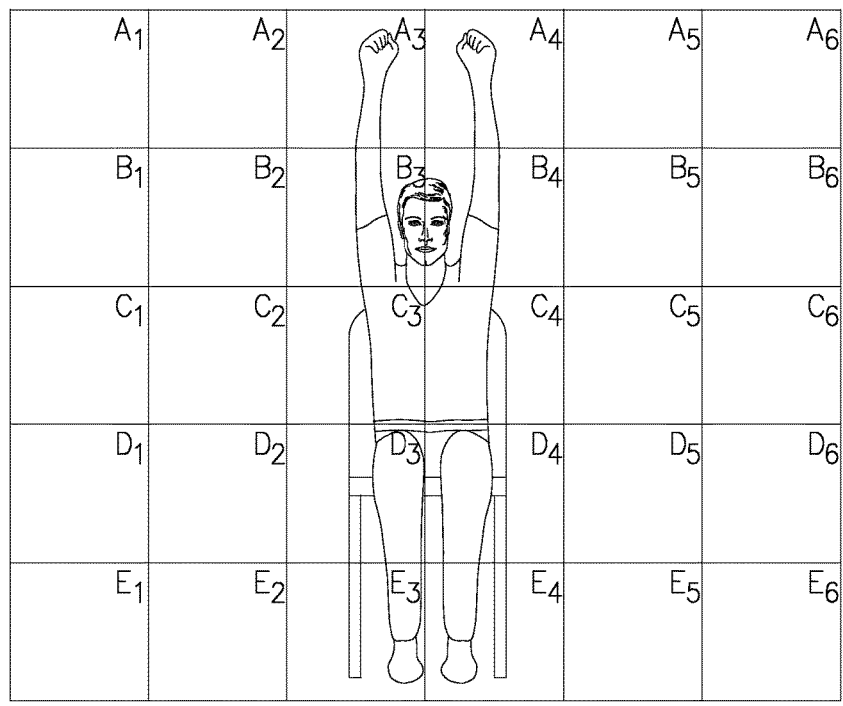
FIG. 6 show diagram depicting an aspect in accordance with some embodiments of the invention.

FIG. 6 shows diagram depicting an aspect in accordance with some embodiments of the invention. A table illustrates a frame of reference in the form of a 5×6 matrix wherein each square is a spatial location such as A2, C5, and D3. The matrix may be extremely useful in quantifying both the abnormality mobility of the patient but also it may serve as a common frame of reference for tailoring sets of exercises for the human patients.

Figure 7:
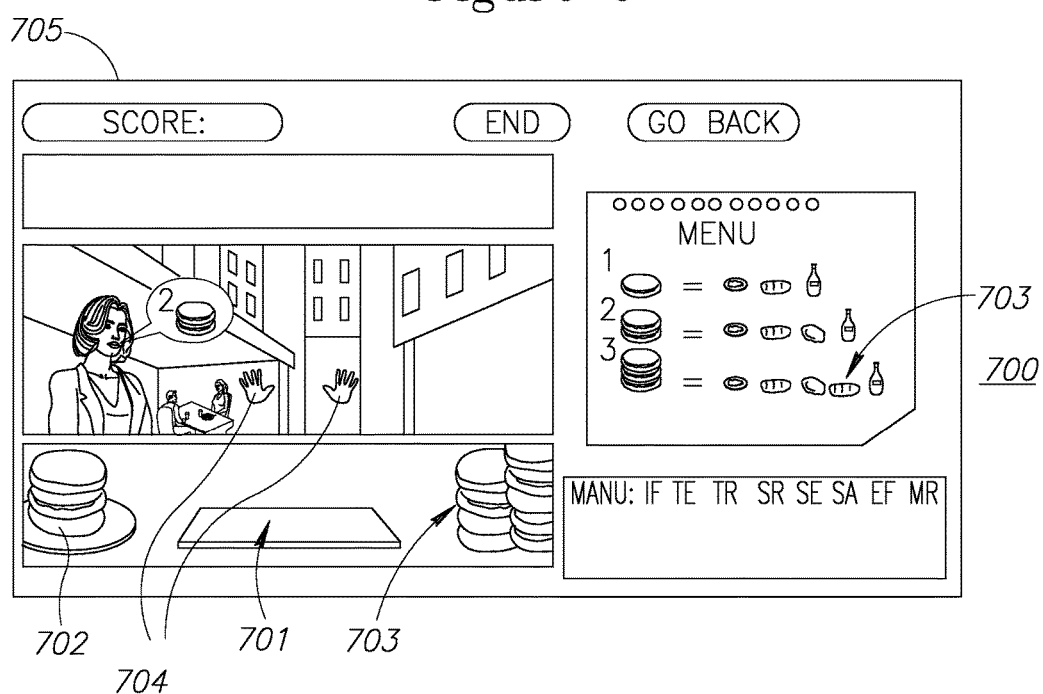
FIG. 7 shows an exemplary graphic user interface depicting an aspect in accordance with some embodiments of the invention.

FIG. 7 shows an exemplary image of a GUI that displays a virtual environment of a food working surface 701 and virtual objects such as buns 703, hamburgers 702, ketchup bottle 706, and lettuce and tomato 705, according to some embodiments of the present invention. During a remote physiotherapy session, the patient is instructed to perform a physical task, to assemble a burger sandwich according to the instructions of a virtual consumer 707, in light of the menu 708. Then, the patient maneuvers his hand as if she holds one or two of a bun, a hamburger, the ketchup bottle, or the lettuce and tomato 705 to assemble the burger sandwich. The hand indicators 704 simulate the location of the hands of the patient during the physical operation he performs, based on the set of 3D movement vectors.

A explained above, embodiments of the present invention provide a client terminal of managing a remote physiotherapy session. The client terminal comprises a display which displays a virtual environment comprising a plurality of elements and instructions which instructs a patient to perform at least one physical task that requires from the patient to perform at least one physical operation to effect at least one of the plurality of elements in the virtual environment, an image sensor which captures a plurality of images depicting the patient performs the at least one physical operation when the patient performs each the at least one physical task, an image processing module which extracts a set of 3D movement vectors by processing the plurality of images, a simulation management module which simulates movement of at least one of the plurality of elements in the virtual environment according to the 3D movement vectors, and a physiotherapy module which identifies at least one biomechanical abnormality by a motion analysis based on the 3D movement vectors and outputs an indication for the at least one biomechanical abnormality.

First, as shown at 301, a virtual environment which simulates a plurality of virtual objects is displayed on the display of the client terminal 102. Optionally, the virtual environment simulates a gaming environment and the plurality of virtual objects are objects which at least one or more of them is maneuvered or otherwise interacted during a game session, in response to one or more gestures of the patient. As shown at 302, the patient is instructed, for example by instructions which appear on the screen and/or in advance, to perform one or more physical operations, such as gestures, for example reaching or moving a virtual object with one or two hands or legs. The physical tasks are selected so as to enhance a targeted movement or targeted exercise of a user which performs the one or more physical operations. The simulated physical tasks may be daily tasks which require daily physical operations, for example maneuvering limbs as if the patient moves certain daily objects, such as food, furniture, and utility devices. The simulated physical tasks may be gaming tasks which require physiotherapy physical operations, for example maneuvering limbs as if the patient has to overcome virtual obstacles or moving certain gaming objects by physiotherapy gestures, for example as described below.

Optionally, the one or more physical tasks are set according to a physiotherapy plan that is selected for the patient according to his disability, his disability level, and/or his progress in previous physiotherapy sessions, or any combination thereof. Optionally, the one or more physical tasks are game tasks, such as achieving a certain score, assembling a certain product, assembling a number of products and the like. Optionally, the one or more physical tasks are prescribed by a clinician as therapeutic exercises to be performed at home. Optionally, games in a certain level or certain game tasks are prescribed as therapeutic exercises to be performed at home. For example, the clinician may prescribe the patient to achieve a certain score, acquiring a certain amount of points in a game, assembling a certain product a certain number of times, moving a certain virtual object via a certain route, and/or performing any other game tasks, such as combining a certain number of burger sandwiches, as described below. The clinician may update the system to instruct the patient to achieve a certain score, acquire a certain amount of points in a game, assemble a certain product a certain number of times, move a certain virtual object via a certain route, and/or perform any other game tasks, such as to combine a certain number of burger sandwiches, as described below.

Optionally, a physical task is set to achieve a repetition of certain physical operations. For example, a physical task may be to assemble a virtual sandwich, a virtual device, or a virtual artifact in a manner that requires from the patient to perform the same gesture a number of times, for example placing a number of virtual objects, in the same place or on top of one other. In such a manner, the patient has more intellectual challenge in the physical task and therefore less weary from it. Optionally, the physical tasks which are set to be performed in a physiotherapy session are different physical tasks which are set to achieve a repetition of the same physical operation, for example a certain gesture or a movement. For example, while one physical task may be to assemble a virtual sandwich in a manner that requires a repetition of a specific gesture, another physical task may be to pass virtual objects from one side to another in a manner that requires from the user to repeat the same specific gesture a number of times. In such a manner, a number of different tasks, which require similar movements, may be presented to the patient sequentially, diversify the physiotherapy session so as to improve the compliance of the patient.

Optionally, the characteristics of the one or more physical tasks are selected or adjusted according to an assessment and performance results of previous physiotherapy sessions practiced using the system 100, for example as described below. The characteristics may be modified by instructions received from a remote clinician, for example as described below. By adjusting the tasks according to previous achievements or progress of the patient, the remote physiotherapy session remains at a challenging level while allowing the patient to perform movements in a correct biomechanical alignment. Optionally, each one of the physiotherapy session modules 105 is to present a graphic user interface (GUI) that allows changing the characteristics of the tasks, for example define launch and landing positions of virtual objects in the virtual environment, the amount of virtual objects in the virtual environment and the speed of virtual objects in the in the virtual environment.

It should be noted that although the above description focuses on physiotherapeutic sessions, embodiments of the invention may be easily implemented in other applications such as the gaming industry in which the abnormality mobility profile may be used in computer games in order to adjust the game to special needs of a player. Similarly, embodiments of the present invention may be used advantageously in training sessions in fitness and health clubs where the abnormality mobility profile may be used to adjust the training session to the people with mobility limitations.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wire-line, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++, C# or the like and conventional procedural programming languages, such as the "C" programming language or any other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The aforementioned flowchart and diagrams illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention.

What is claimed is:

1. A system comprising:
   one or more two-dimensional or three-dimensional cameras configured to capture images depicting a human patient, over a calibration session, including 3D positioning and orientation of body parts of a human patient, wherein the human patient is instructed to follow a sequence of movements in said calibration session; and
   a computer processor configured to:
      monitor over the calibration session, a set of key points depicted in the captured images, wherein at least some of the key points are located in locations on the body parts of the human patient;
      generate an abnormality mobility profile of the human patient by analyzing the monitored set of key points depicted in the images in view of deviations from predefined quantitative measures, wherein the abnormality mobility profile is indicative of mobility limitations and compensatory movements of the human patient,
   wherein the one or more cameras are further configured to capture additional images in a physiotherapeutic or training session that depict 3D positioning and orientations of the body parts of the human patient over time,
   wherein the computer processor is further configured to:
      monitor, over the physiotherapeutic or training session, the set of key points on the human patient depicted in the captured additional images while the human patient performs physical training or physiotherapeutic exercises comprising a set of predefined sequences of body-related and limb-related postures and gestures; and
      analyze the monitored set of key points during the physical training or physiotherapeutic session, to yield an assessment of a level of compliance of the human patient in performing the physiotherapeutic exercises, based at least partially on the abnormality mobility profile; and instructing the human patient, during the calibration session, to follow a set of predefined sequences of postures and gestures and wherein the abnormality mobility profile is generated at least partially based on a comparison between the calibrated key points of the human patient responsive to the predefined sequences of postures and gestures and respective monitored key points of the healthy human responsive to the predefined sequences of postures and gestures.

2. The system according to claim 1, wherein the computer processor is configured to generate a set of physical training or physiotherapeutic exercises tailored for the human patient's motor capabilities based on the abnormality mobility profile and additional input from a human expert.

3. The system according to claim 1, wherein the capturing of the physiotherapeutic sequence and the analyzing of the monitored set of key points during the physiotherapeutic session are carried out at different locations.

4. The system according to claim 1, wherein the capturing of the physiotherapeutic sequence is carried out at one or more different locations, wherein in each one of the different locations, a different human patient is following a tailored set of exercises, and wherein the assessment of at least some of the different human patients is presented to a human expert in real time.

5. The system according to claim 4, wherein the computer processor is further configured to provide a quantitative score indicative of the human patient compliance with the physiotherapeutic session, wherein the score is based on a comparison to a predefined database.

6. The system according to claim 4, wherein the computer processor is configured to provide at least one of: feedback, exercise adjustments, and recommendations to the human patient, based on the assessment of the level of compliance of the human patient in performing the physical training or physiotherapeutic exercises.

7. The system according to claim 6, wherein the presenting of the assessment of level of compliance of the human patient in performing the physical training or physiotherapeutic exercises of at least some of the different human patients is carried out in accordance of a dynamic prioritization process.

8. The system according to claim 7, wherein the abnormality mobility profile of the human patient takes into account a complete representation of skeleton trajectories of the human patient, such that the feedback, the exercise adjustments, and the recommendations only promote exercises that are beneficial for the physical training or physiotherapeutic session of the human patient.

* * * * *